x
US008124355B2

(12) United States Patent
Miller

(10) Patent No.: US 8,124,355 B2
(45) Date of Patent: Feb. 28, 2012

(54) DETECTION AND IDENTIFICATION OF GROUPS OF BACTERIA

(75) Inventor: Stefan Miller, Regensburg (DE)

(73) Assignee: Biomerieux S.A., Marcy l'Etoile (FR)

( * ) Notice: Subject to any disclaimer, the term of this patent is extended or adjusted under 35 U.S.C. 154(b) by 2014 days.

(21) Appl. No.: 10/470,797

(22) PCT Filed: Feb. 1, 2001

(86) PCT No.: PCT/DE01/00431
§ 371 (c)(1),
(2), (4) Date: Feb. 17, 2004

(87) PCT Pub. No.: WO02/061117
PCT Pub. Date: Aug. 8, 2002

(65) Prior Publication Data
US 2004/0121403 A1    Jun. 24, 2004

(51) Int. Cl.
*C12Q 1/00* (2006.01)
*C12Q 1/70* (2006.01)
*G01N 33/53* (2006.01)
*G01N 33/567* (2006.01)
*G01N 33/554* (2006.01)
*G01N 33/569* (2006.01)
*G01N 33/542* (2006.01)
*G01N 33/00* (2006.01)
*C12N 7/00* (2006.01)

(52) U.S. Cl. ............... 435/7.2; 435/4; 435/5; 435/7.1; 435/7.32; 435/7.8; 435/7.9; 435/7.92; 435/7.93; 435/235.1

(58) Field of Classification Search ............... 435/7.1, 435/7.2, 7.32, 7.8, 7.9, 7.92, 7.93, 235.1; 530/300, 350, 387.1, 387.3, 412
See application file for complete search history.

(56) References Cited

U.S. PATENT DOCUMENTS

| 5,864,013 | A  | * | 1/1999 | Goldberg .................. 530/350 |
| 5,958,675 | A  | * | 9/1999 | Wicks et al. ................. 435/5 |
| 2003/0017449 | A1 | * | 1/2003 | Adams et al. ................. 435/5 |
| 2004/0191892 | A1 | * | 9/2004 | Wicks et al. ............... 435/288.2 |

FOREIGN PATENT DOCUMENTS

| WO | WO/9317129 |   | 2/1993 |
| WO | WO 93/17129 | * | 9/1993 |
| WO | WO/0109370 |   | 2/2001 |

OTHER PUBLICATIONS

Bennett et al (The use of bacteriophage-based systems for the separation and concentration of *Salmonella*, Journal of Applied Microbiology, 1997; 83(2): 259-265).*

Bennett et al (The use of bacteriophage-based systems for the separation and concentration of *Salmonella*, Journal of Applied Microbiology, 1997; 83: 259-265).*
Thomas E. Creighton, in his book, "Proteins: Structures and Molecular Properties, 1984", (pp. 314-315).*
Creighton, in his book Protein Structure: A Practical Approach, 1989; pp. 184-186.*
Nosoh, Y. et al in "Protein Stability and Stabilization through Protein Engineering, 1991" (chapter 7, p. 197, second paragraph).*
Kumar, V. et al (Amino acid variations at a single residue in an autoimmune peptide profoundly affect its properties: T-cells activation . . . , Immunology, 1990; 87: 1337-1341).*
UniProtKB/TrEMBL entry Q38160, http://ca.expasy.org/uniprot/Q38160, pp. 1-2, Nov. 1, 1996.*
Selivanov et al, Nucleotide and deduced amino acid sequence of bacteriophage T4 gene 12, Nucleic Acids Research, 1988; 16(5): 2334.*
Bennett et al., "The use of bacteriophage-based systems for the separtation and concentration of *Salmonella*," *Journal of Applied Microbiology*, 83(2):259-265, 1997.
Mesyanzhinov, "Bacteriophage T2 gene for gp12," *Database EMBL Online!*, XP002187843, 1992.
Mesyanzhinov, "Enterobacteria phage T4," *Database EMBL Online!*, XP002187844, 1988.
Selivanov et al., "Nucleotide and deduced amnio acid sequence of bacteriophage T4 gene 12," *Nucleic Acids Research*, 16(5) part B, 2334, 1988.
Burba and Miller, "Folding of coliphage T4 short tail fiber in vitro," *Eur. J. Biochem.*, 265:771-778, 1999.
Burba et al., "Stability of bacteriophage T4 short tail fiber," *Biol. Chem.*, 381:255-258, 2000.
Chen and King, "Thermal unfolding pathway for the thermostable P22 tailspike endorhamnosidase," *Biochemistry*, 30(25):6260-6269, 1991.
Danner et al., "Folding and assembly of phage P22 tailspike endorhamnosidase lacking the N-terminal, head-binding domain," *Eur. J. Biochem.*, 215:653-661, 1993.
Grabarek and Gergely, "Zero-length crosslinking procedure with the use of active esters," *Analytical Biochemistry*, 185:131-135, 1990.
Mur, "2,4,6-Trichloro- 1,3,5-triazine (cyanuryl chloride) and its future applications," *Russian Chemical Reviews*, 33(2):92-103, 1964.

* cited by examiner

*Primary Examiner* — Gary Nickol
*Assistant Examiner* — Lakia Tongue
(74) *Attorney, Agent, or Firm* — Fulbright & Jaworski

(57) ABSTRACT

The present invention concerns a method for the simultaneous detection of different bacteria, comprising the following steps: coupling one or more species of bacteriophage tail proteins onto a support, incubating the support coupled with the bacteriophage tail proteins with a sample, optionally removing the sample and the bacteria of the sample not bound to the bacteriophage tail proteins, contacting the bacteria bound to the bacteriophage tail proteins with the bacteriophages and/or bacteriophage proteins specifically binding the bacteria to be detected, removing the bacteriophages and/or bacteriophage proteins not bound to the bacteria, and performing the detection reaction by means of an enzyme coupled to the specifically binding bacteriophages and/or bacteriophage proteins or by means of an immuno assay.

25 Claims, 4 Drawing Sheets

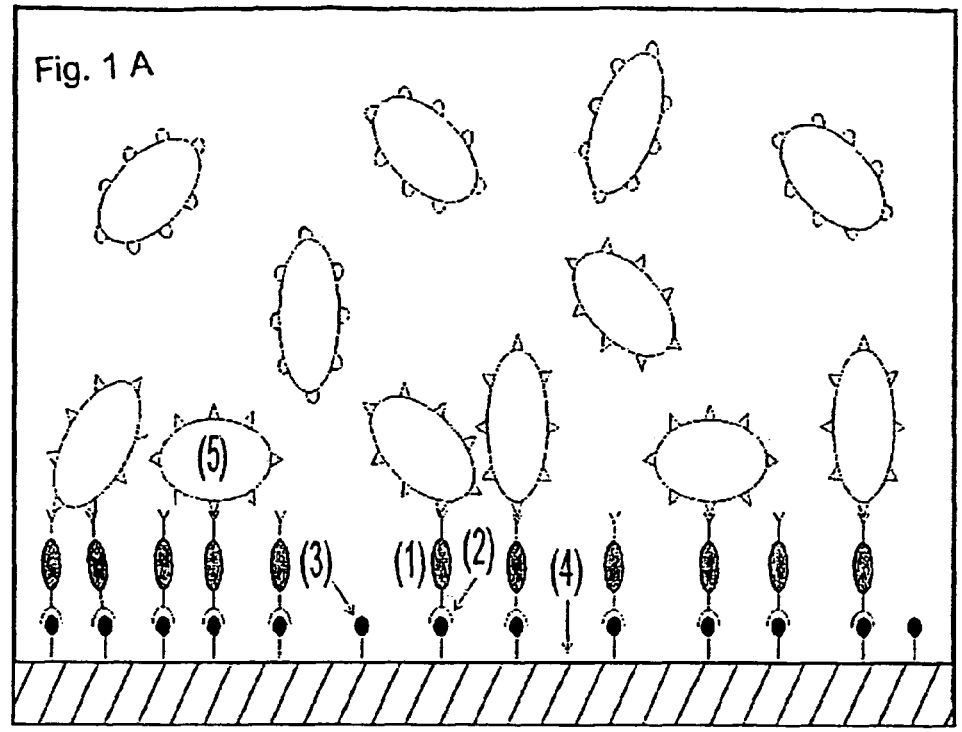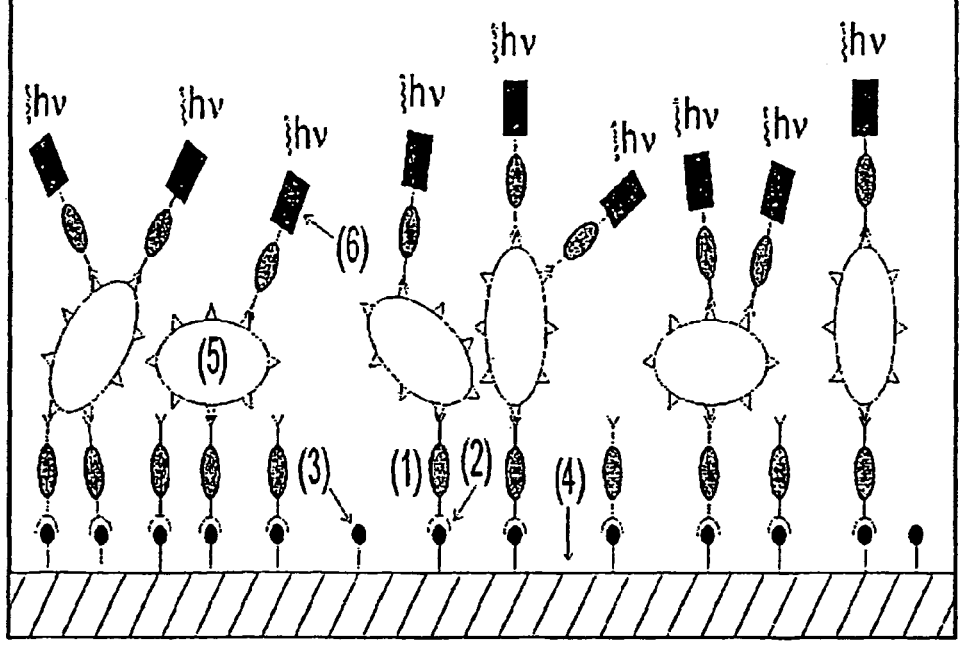
FIG. 1A-B

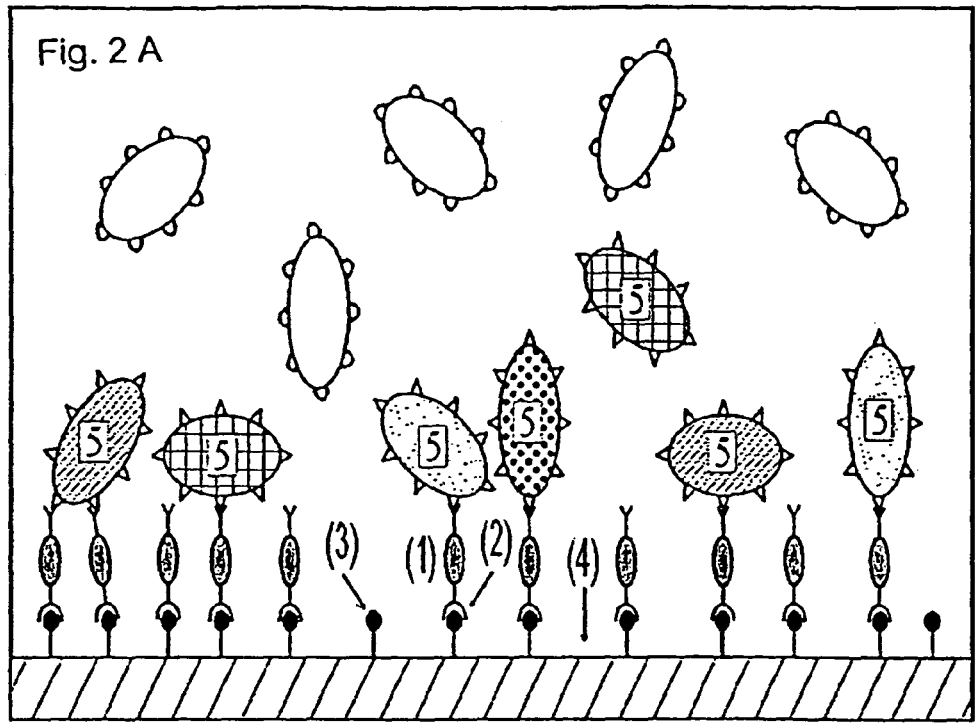
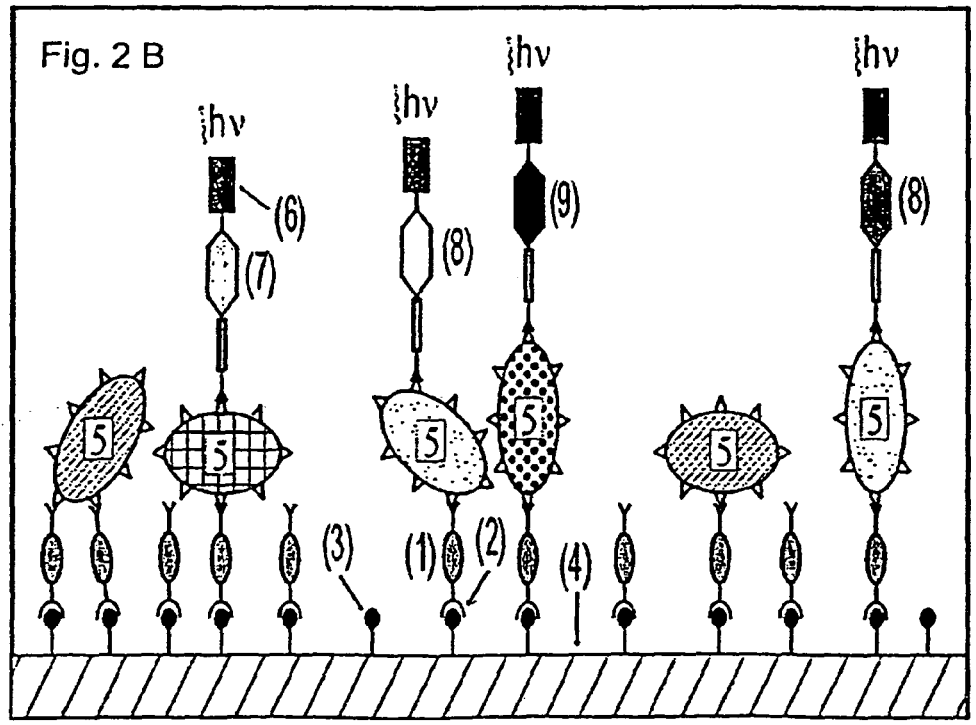
FIG. 2A-B

Fig. 3 A

```
            agtaata atacatatca acacgtttct aatgaatctc gttatgtaaa
   51   atttgatcct accgatacga attttccacc ggagattact gatgttcacg
  101   ctgctatagc agccatttct cctgctggCg taaatggagt tcctgatgca
  151   tcgtcaacaa caagggaat tTtatttCtt Gccactgaac aggaagttat
  201   agatggaact aataatacca aagcagttac accagcaacg ttggcaacaa
  251   gattatcAta tccaaaCgca actgaaaGtg tttacggatt aacaagatat
  301   tcaaccGatg atgaagccat tgccggagtt aataatgaat cttctataac
  351   tccagctaaa tttactgtTg cTcttaataa tgTTtttgaa acTcgTgttt
  401   caactgaatc AtcaaatggG gttattaaaa tttcatctTt accgcaagca
  451   ttGgcAggtg cagatgatac tactgcaatg actccattaa aaacacaAca
  501   AttagctGtt aaattGattg cgcaaattgc tccttctAaa aATGcTgcta
  551   cAgaatcTga GcaaggtgtA AttcaGttag cTacagtagc AcaggCtcgt
  601   cagggaactt taagagaagg AtaCgcaatt tctccttata cgtttatgaa
  651   ttcTActGct actgaagaat ataaaggcgt aattaaatta ggaacGcaat
  701   cagaagttaa ctcgaataat gcttctgttg cggttactgg Agcaactctt
  751   aatggtcgtg gttctacgac gtcaatgaga ggcgtagtta aattaactac
  801   aaccgccggt tcacagagtg gaggcgatgc ttcatcagcc ttagcttgga
  851   atgctgacgt tatccaCcaa agaggCggtc aaaCtatTAa tggaacactT
  901   cgcattAaTA aTacGCttac aatagctTCA ggtggGgcaa atattacCgg
  951   AacAgtTaAC atgactggcg gttatattca aggtaaAcgc Gtcgtaacac
 1001   aaaatgaaat tgatagaact attcctgtcg gagctattat gatgtgggcc
 1051   gctgatagtc ttcctagtga tgcttggcgT ttTtgccaCg gtggaactgt
 1101   ttcagcgtca gattgtccat tatatgcttc tagaattgga acaagatatg
 1151   gcggaaGcTc atcaaatcct ggattgcctg acatgcgCgg tcttttttgtt
 1201   cgtggCtctg gCcgtggCtc tcaTttaaca aatccaaatg ttaatggtaa
 1251   tgaccaattt ggtaaaccta gattaggtgt aggttgtacT ggtggatatg
 1301   ttggtgaagt acagaAacaa cagatgtctt atcataaaca tgctggtgga
 1351   tttggtgagT atgatgatTC Tggggcattc ggtaatacTc gtagatcaaa
 1401   ttttgttggt acacgtaaag gacttgactg ggataaccgt tcatacttca
 1451   cTaatgacgg Gtatgaaatt gacccagCat cacaacgaaa ttccaGatat
 1501   acattaaatc gtcctgaatt aattggaaat gaaacacgtc catggaacat
 1551   ttctttaaac tacataatta aggtaaaaga a
```

FIG. 3A

Fig. 3 B

```
MSNNTYQHVS NESRYVKFDP TDTNFPPEIT DVHAAIAAIS
PAGVNGVPDA SSTTKGILFL ATEQEVIDGT NNTKAVTPAT
LATRLSYPNA TESVYGLTRY STDDEAIAGV NNESSITPAK
FTVALNNVFE TRVSTESSNG VIKISSLPQA LAGADDTTAM
TPLKTQQLAV KLIAQIAPSK NAATESEQGV IQLATVAQAR
QGTLREGYAI SPYTFMNSTA TEEYKGVIKL GTQSEVNSNN
ASVAVTGATL NGRGSTTSMR GVVKLTTTAG SQSGGDASSA
LAWNADVIHQ RGGQTINGTL RINNTLTIAS GGANITGTVN
MTGGYIQGKR VVTQNEIDRT IPVGAIMMWA ADSLPSDAWR
FCHGGTVSAS DCPLYASRIG TRYGGSSSNP GLPDMRGLFV
RGSGRGSHLT NPNVNGNDQF GKPRLGVGCT GGYVGEVQKQ
QMSYHKHAGG FGEYDDSGAF GNTRRSNFVG TRKGLDWDNR
SYFTNDGYEI DPASQRNSRY TLNRPELIGN ETRPWNISLN
YIIKVKE
```

DETECTION AND IDENTIFICATION OF GROUPS OF BACTERIA

This application claims priority to PCT/DE 01/0431, filed on Feb. 1, 2001. The entire content of this application is incorporated by reference.

The present invention concerns a method for the simultaneous detection of different bacteria, comprising the following steps: coupling one or more species of bacteriophage tail proteins onto a support, incubating the support coupled with the bacteriophage tail proteins with a sample, optionally removing the sample and the bacteria of the sample not bound to the bacteriophage tail proteins, contacting the bacteria bound to the bacteriophage tail proteins with the bacteriophages and/or bacteriophage proteins specifically binding the bacteria to be detected, removing the bacteriophages and/or bacteriophage proteins not bound to the bacteria, and performing the detection reaction by means of an enzyme coupled to the specifically binding bacteriophages and/or bacteriophage proteins or by means of an immuno assay.

The rapid and precise detection of bacteria is absolutely essential for checking the hygiene and quality aspects of raw products and processed foodstuffs and for monitoring the hygiene and quality aspect of drinking water and water for industrial uses and the water quality of public baths. In addition detection serves for process monitoring and optimisation as well as quality control in environmental analysis.

In spite of the enormous economic interest the test methods used at the present time such as for example the "BAM" methods (bacteriological analytical manual) are very intensive in terms of time, labour and equipment. Potential disease germs are sequentially augmented in selective and non-selective media and detected on suitable nutrient media. That is usually followed by biochemical and serological checking so that the entire method takes between 3 and 4 days. For certain situations, for example in relation to hygiene monitoring, it may be necessary to detect entire groups of bacteria, instead of individual bacterial species. That however can also be important when for example the proportion of pathogenic bacteria in a group is very great. The tests can only be carried out by microbiologically trained personnel in suitably equipped laboratories. The consequence of this is that at the present time even large undertakings only test coliform bacteria in house but outsource all other tests, including detection of pathogenic germs. Coliform detection is essentially used as hygiene monitoring, it is generally implemented by way of conventional nutrient medium procedures and thus lasts at least two days.

The detection of bacteria is mostly effected from biological samples by means of a combination of culture methods. In addition, particularly for precise characterisation, recourse is had to the procedure of phage typing. In that situation culture methods are coupled to the sensitivity of bacteria in relation to typing bacteriophages. Bacteriophages have already been used for about 80 years in phage typing, in which bacteria strains can be determined by means of special classification phages on the basis of standardised systems. A dense bacteria layer on an agar plate of the sample to be investigated, which was obtained by isolation of an individual colony and subsequent multiplication thereof, is coated with suspension of bacteriophages in soft agar. The result is obtained after incubation overnight at the optimum growth temperature of the bacteria, which is usually generally 37° C., by counting out the plaques and checking the plaque morphology.

More recent alternative methods which make do without a nutrient medium are based in particular on DNA and antibody technologies. In the first-mentioned approach the bacteria are bound to filters and the bacteria DNA hybridised with suitable DNA probes which give a measurement signal or the amplified bacteria DNA is directly sequenced on by means of PCR. In the ELISA procedure bacteria or bacteria constituents are bound by means of monoclonal antibodies and detected by way of enzymatic probes which are coupled to a secondary antibody. Both methods however also require a high level of technical expenditure and an enrichment step is to be implemented beforehand for the required $10^4$ to $10^6$ cells per ml. This means that the time saving in comparison with conventional methods is so small that the stated methods are scarcely used.

The use of bacteriophages as "biosorbents" for binding of the bacteria to be detected has some decisive advantages over the more recent methods. The phage-bacteria systems have evolved in nature over long periods of time so that the phages recognise their host bacteria in highly specific fashion and with a high level of binding affinity even in complex environments as occur in nature but also in foodstuffs. Time-consuming enrichment cultures in which the germs which are unwanted for the detection procedure such as for example inoculation cultures are frequently also enriched become substantially unnecessary by virtue of the novel method described here. A disadvantage with the previously described phage-based bacteria detection systems however is that they mostly involved highly specific recognition of individual bacterial species and therefore cannot be used for detection of bacteria groups, families or a plurality of species of bacteria.

Therefore the object of the present invention is to provide a detection method for bacteria, with which different bacteria species can be simultaneously detected. A further object involves the provision of bacteriophage tail proteins which have bacteria binding which is more advantageous for the detection method.

The object is solved by the subject-matter defined in the claims.

The invention is described by the following Figures.

FIGS. 1A and B diagrammatically show group-specific detection. (1A): the bacteriophage tail protein 1 is bound by way of biotin 2 to streptavidin 3 which is covalently joined to the matrix 4. Bacteria from the group 5 to be recognised are specifically bound to the bacteriophage tail proteins 1. (1B): after a washing step the bound bacteria 5 are detected by means of the same bacteriophage tail protein 1 which however this time is coupled to an enzyme 6, for example peroxidase. hv denotes signal development which can be implemented for example by absorption.

FIGS. 2A and B diagrammatically show group-specific detection. (2A): the bacteriophage tail protein 1 is bound by way of biotin 2 to streptavidin 3 which is covalently joined to the matrix 4. Bacteria from the group 5 to be recognised are specifically bound to the bacteriophage tail proteins 1. (2B): after a washing step the bound bacteria 5 are detected by means of strain-specific bacteriophages 7, 8, 9 which are coupled to an enzyme 6, for example peroxidase. hv denotes signal development which can be implemented for example by absorption.

FIG. 3A shows the DNA sequence of the short tail fibres p12 of the phage strain T4D (SEQ ID NO: 2). FIG. 3B shows the amino acid sequence of that variant (SEQ ID NO: 1). The nucleic acid sequence in accordance with SEQ ID NO: 4 and the amino acid sequence in accordance with SEQ ID NO: 3 are underlined. Capitals in the nucleic acid sequence represent base exchanges in relation to wild type sequence T4 p12 (Swiss-Prot. accession number P10930).

The term "coliform" used herein denotes a subgroup of the enterobacteria which are distinguished in that they utilise lactose and express the enzyme β-galactosidase, respectively.

The term "bacteria group" used herein denotes a summarization of specific bacteria which can be within a family, or a genus, or a species etc., but can also be spanning.

The term "derivative" used herein denotes nucleic acid or amino acid sequences which in relation to the comparative sequence exhibit modifications in the form of one or more deletions, substitutions, additions, insertions and/or inversions.

The term "fragments" used herein denotes parts of amino acid sequences and the nucleic acid sequences coding for those amino acid sequence as long as they exhibit the biological function of the amino acid sequences according to the invention.

One aspect of the present invention therefore lies in the provision of a method for the simultaneous detection of different bacteria including the following steps: coupling one or more species of bacteriophage tail proteins onto a support, incubating the support coupled with the bacteriophage tail proteins with a sample, optionally removing the sample and the bacteria of the sample which are not bound to the bacteriophage tail proteins, contacting the bacteria bound to the bacteriophage tail proteins with bacteriophages and/or bacteriophage proteins specifically binding the bacteria to be detected, removing the bacteriophages and/or bacteriophage proteins not bound to the bacteria, and performing the detection reaction by means of an enzyme coupled to the specifically binding bacteriophages and/or bacteriophage proteins or by means of an immuno assay. Alternatively detection can be effected by way of (bacterial) cellular enzymes (for example β-galactosidase in the case of coliforms) or also other cell constituents such as nucleic acids, proteins, lipids or sugar components.

Bacteriophage tail proteins which are specific for the desired bacteria to be detected are used for the method according to the invention. In this respect the bacteriophage tail proteins are specific for a plurality of bacteria species. The bacteria to be detected can be for example entire bacteria families, one or more entire bacteria genera, given bacteria species from a bacteria genus, given bacteria species from a plurality of bacteria genera, or the like. The bacteria to be detected with the method according to the invention can originate for example from the family of enterobacteriaceae. Preferably bacteria are detected from the genus *Escherichia, Salmonella, Shigella, Klebsiella, Enterobacter, Citrobacter, Proteus, Serratia, Morganella, Providencia, Yersinia, Hafnia* and/or *Edwardsiella*, particularly preferably from *Escherichia, Salmonella, Shigella, Klebsiella, Enterobacter* and/or *Citrobacter*. Further preferably bacteria to be detected are the species *Escherichia* spec., *Salmonella* spec., *Shigella* spec., *Klebsiella* spec., *Enterobacter* spec., *Citrobacter* spec., *Proteus* spec., *Serratia* spec., *Morganella* spec., *Providencia* spec., *Yersinia* spec., *Hafnia* spec., *Edwardsiella* spec. and/or *Pseudomonas* spec.

By way of example it is irrelevant for the user for example in the milk or drinks industry for bacterial contaminations to be characterised serologically and strain-specifically. What is important is only the general information as to whether for example in the production procedure foreign germs had gained access into the installation or germ sterilisation processes were successful. Coliform bacteria serve in that respect generally as a hygiene indicator. Thus a particular embodiment of the method according to the invention is the detection of coliform bacteria, in particular of the genera *Escherichia, Salmonella, Shigella, Klebsiella, Enterobacter, Citrobacter, Proteus, Serratia, Morganella, Providencia, Yersinia*, and/or *Hafnia edwardsiella*.

Which bacteriophage tail proteins are used depends on which bacteria species, groups or families are to be detected. Group-specific detection in accordance with the invention involves using those bacteriophage tail proteins which recognise and bind group-specific receptors. In that case it is possible to use any phage tail protein which has a corresponding recognition spectrum. Preferred phage tail proteins are those from the family of Myoviridae, Podoviridae and Siphoviridae, in particular short phage tail proteins, in particular the short phage tail proteins of the "even-numbered T-phages", for example of T4, T2 or K3, in particular the bacteriophage tail protein p12 from T4, p12 from T2 (GenBank Accession Number X56555), p12 from K3 (see Burda et al., 2000, Biol. Chem. Vol. 381, pp 255-258), or the bacteriophage tail proteins of the phages felix 01, P1 or PB1. In that respect for example the short bacteriophage tail proteins of the phages T4 (p12) and P1 bind to coliforms, the short phage tail protein of felix 01 binds to Salmonellae and the short phage tail protein of PB1 binds to Pseudomonadae. For example the Salmonellaphage Felix 01 (F01) recognises up to 99% of all Salmonellae and can be used for group-specific Salmonella detection. The bacteriophage tail proteins of PB1 can be used for group-specific Pseudomonada detection.

How the bacteriophage tail proteins are intended to bind to the individual bacteria is to be made clear here by way of example with reference to the "even-numbered T-phages" for example T4, T2 and K3. In this group on the host side there are two components which are recognised by the phages: firstly a surface protein which is specific for individual phages and secondly the lipopolysaccharide (LPS) which all gram-negative bacteria have in modified form. The long tail fibres of the "even-numbered T-phages" play a part in specific recognition of the host bacteria while the LPS serves as a receptor for the short tail fibres. It is known in regard to *E. coli* phages T4 that the specific interaction afforded by the long tail fibres with the host bacterium becomes irreversible as soon as the short tail fibres have also bound to the bacteria surface. The short tail fibre is not responsible for precise specificity within the host bacteria group and can therefore be interchanged between the various "even-numbered T-phages".

The short tail fibres are involved together with the tail pins in the so-called pinning step in which irreversible binding of the phage to LPS takes place on the host surface. p12 requires for binding to LPS a structure of heptose sugars with at least one α-bound glucose, as is to be found in the inner core zone of the cell wall of enterobacteria. Differing phosphorylation of the sugars, as frequently occur, the presence of substitutions with pyrophosphatidylethanolamine or also the branchings of the heptose region do not appear to play any part. Although the lipopolysaccharides of the individual bacteria strains in the O-specific side chains—which is used for serological typing—but also in the outer core regions are very greatly different the variance in the inner core region is very much less pronounced. All enterobacterial core regions have for example the following two sugars: 3-desoxy-D-manno-octuronic acid (Kdo) and L-glycero-D-manno-heptopyranose (Hep) which provide the following characteristic oligosaccharide in the inner core zone:

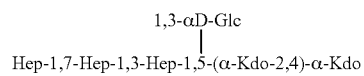

The central heptose is generally substituted at O3 and carries inter alia in the case of *Escherichia coli*, as well as in the case of *Salmonella enterica, Shigella* spp., *Hafnia* spp., *Citrobacter* spp. and *Erwinia* spp., a 1,3-bound αD-glucose. Klebsiella, Proteus and Yersinia have at that position either galactose or an N-acetyl fucosamine and are not recognised by p12. Klebsiella is however recognised for example by the short bacteriophage tail protein of the phage P1.

Bacteriophage tail proteins, their derivatives, variants or fragments can be produced in easily recombinant fashion in large amounts and isolated. However, for the method according to the invention it is possible to use not only the naturally occurring bacteriophage tail proteins but also their variants. The expression "variants" denotes in accordance with the present invention that the bacteriophage tail proteins have an altered amino acid sequence in relation to the wild type sequence. Naturally occurring variants can be found by conventional screening methods. The variants also further include synthetically produced bacteriophage tail proteins. The synthetically produced polypeptides can be produced for example by targeted or random mutagenesis. Mutagenesis makes it possible to introduce modifications which can be amino acid additions, deletions, substitutions, inversions or insertions. The bacteriophage tail proteins can further have chemical modifications such as for example methylations or acetylations. The modifications can implement an altered and in particular an improved host specificity and also an improved binding property to the matrix, for example can increase the binding of the bacteria to the isolated phage proteins or make it irreversible in order to improve the washing options.

In addition it is also possible to use two or more bacteriophage tail proteins in a detection method if the bacteria to be detected cannot be detected by a single bacteriophage tail protein. For example it is possible to use the short bacteriophage tail proteins of the phages T4 (p12) and P1 which have a slightly different host spectrum in order at the same time, besides the bacteria genera recognised by both bacteriophage tail proteins *Escherichia, Salmonella, Shigella, Citrobacter* and *Erwinia*, to detect the genus *Hafnia* recognised only by T4 p12 and the genera *Klebsiella* and *Enterobacter* recognised only by the short bacteriophage tail protein of the phage P1. In addition for the detection of Salmonellae it may be advantageous to use the short phage tail protein of felix 01 with other bacteriophage tail proteins as at the present time 2500 *Salmonella* serovars (subtypes of bacteria which can be distinguished on the basis of serological features, for example LPS-variations in the O-antigen) are described. Which bacteriophage tail proteins are used for the detection procedure ultimately depends on which bacteria species, groups or families are to be detected.

Preferably the bacteriophage tail protein is a variant of the wild type p12 protein in accordance with SEQ ID NO: 1, particularly preferably in accordance with SEQ ID NO: 3. The invention further concerns the nucleic acid sequences in accordance with SEQ ID NO: 2 and 4.

SEQ ID NO: 1 represents the amino acid sequence of the naturally occurring p12-variant, namely T4D p12. That bacteriophage tail protein has for example a very high level of stability in relation to heat (denaturation central point: 78° C.) and chemical denaturation agents (Burda et al., 2000, Biol. Chem., Vol. 381 pp 255-258).

It was surprisingly found that a protease-resistant fragment of that p12-variant binds about 10 times more firmly to bacteria cells, in comparison with the complete p12 proteins. In addition the temperature-sensitive N-terminus of the complete p12-variant is broken down by protease digestion so that the protease-resistant fragment has inter alia a greater degree of long-term stability. The amino acid sequence of the protease-resistant fragment is listed in SEQ ID NO: 3, the nucleic acid sequence in SEQ ID NO: 4. An aspect of the present invention therefore concerns the amino acid sequence in accordance with SEQ ID NO: 3 or the derivatives thereof, and the nucleic acid sequence in accordance with SEQ ID NO: 4 or derivatives thereof. A further aspect of the present invention further concerns fragments and derivatives thereof in accordance with SEQ ID NO: 1, preferably with the sequence of the amino acid radicals 1-500, 1-450, 40-500, 40-450, 270-400, 270-390, 280-400 and 280-390, particularly preferred is the fragment in accordance with SEQ ID NO: 3 as well as the nucleic acid sequences coding for the respective fragments and derivatives.

A further aspect of the present invention concerns poly- and monoclonal antibodies against the amino acid sequence in accordance with SEQ ID NO: 3.

For the detection procedure according to the invention the bacteriophage tail proteins are immobilised on suitable support structures, for example microtiter plates, test strips, slides, wafers, filter materials or through-flow cell chambers. The support structures can for example comprise polystyrene, polypropylene, polycarbonate, PMMA, cellulose acetate, nitrocellulose, glass or silicon wafer. Immobilisation can be achieved for example by adsorption or covalent bonding. What is important in that respect is functional immobilisation, that is to say bacteriophage tail proteins have structures accessible for bacteria, in spite of the binding to the support material.

For suppressing a non-specific reaction of the bacteria to be investigated with the support material it is possible to implement blocking with bovine serum albumin or Tween 20 or similar substances known from the ELISA region, for example milk powder. In addition to enhance the efficiency of adsorption the support systems can be pre-coated with suitable proteins (for example specific antibodies against phage proteins or non-specific proteins such as for example bovine serum albumin), peptides, saccharides (for example mono-, oligo- or polysaccharides) or detergents (for example Tween 20 or octylglucoside). Those coatings can be produced for example either overnight at a temperature in the range of 4-20° C. or in 2-4 h at 30-65° C. Then the excess liquid is removed and the support structure dried at about 60-70° C. The base coating is intended on the one hand to ensure adsorption of the bacteriophage tail proteins and on the other hand to prevent non-specific adsorption of the test bacteria to the support structure in order to enhance the level of test efficiency.

Subsequently to the base coating the bacteriophage tail proteins are applied. For that purpose an aqueous buffered solution of the bacteriophage tail proteins is applied to the pretreated support structure. After adsorption for example at 4-20° C. overnight or at 30-65° C. for 2-4 h the coating solution is removed and the support structure dried as described above. In order to increase the level of coating efficiency it is possible subsequently to implement covalent fixing of the bacteriophage tail proteins with chemical crosslinkers such as for example glutaraldehyde.

Immobilisation of the bacteriophage tail proteins to the support material by means of adsorption can be effected by incubation of a phage solution in aqueous buffer, for example 100 mM tris ph 7.3 or 100 mM sodium phosphate ph 7.5, over several hours or overnight at between 5° C. and 45° C., preferably at between 15° C. and 37° C., particularly preferably at between 20° C. and 37° C., particularly preferably at ambient temperature.

In addition the bacteriophage tail proteins do not have to be immobilised directly on the support but can bind to polypeptides which in turn were immobilised on the support. Those polypeptides can be, being specific for the bacteriophage tail proteins, antibodies, lectins, receptors or anticalins. In addition the bacteriophage tail proteins can be linked to low-molecular substances, for example biotin, in order by way of those low-molecular substances to bind to polypeptides, for example streptavidin, which in turn were immobilised on the support. In that respect, as described hereinbefore, in regard to the bacteriophage tail proteins, the other polypeptides can bind to the support.

In regard to covalent coupling the bacteriophage tail proteins can be coupled for example by way of primary amino groups or carboxyl groups to support materials already activated by the manufacturer, for example microtiter plates from Nunc, Xenobind or Costar, by way of standard conditions, for example —$NH_2$ by way of cyanuryl chloride (Russian Chemical Rev., 1964, 33: 92-103), or —$COO^-$ by way of EDC (1-ethyl-3'[3'-dimethylaminopropyl]carbodiimide) (Anal. Biochem. 1990, 185: 131-135). In addition the support materials can be directly activated with suitable procedures. One possibility which is preferred by virtue of the applicability for a wide spectrum of support materials is silanisation of the support material. For example silanisation in the case of polystyrene can be implemented by flame pyrolysis. Suitable bonding agents are then applied, which permit coupling by way of for example primary amino groups or carboxyl groups.

For binding of the bacteria to be investigated to the immobilised bacteriophage tail proteins the sample being investigated is brought into contact in aqueous form with the bacteriophage tail proteins and incubated. Incubation is effected at a temperature in the range of between 4° and 90° C., preferably at a temperature in the range of between 4° and 45° C., particularly preferably at a temperature in the range of between 15° and 37° C., especially preferably at a temperature in the range of between 20° and 37° C., more particularly at ambient temperature, for up to 6 hours, preferably up to 4 hours, particularly preferably 2 hours, in particular 1 hour, particularly preferably between 1 and 20 minutes. For example incubation can be effected for between 2 and 120 minutes at between 4° and 37° C., preferably for between 20 and 30 minutes at 25° C. or 37° C., particularly preferably for 35 minutes at 37° C. After specific recognition and firm binding of the bacteria non-specifically bound material can be removed by washing with aqueous buffer, for example with PBS or PBS-Tween™ (surfactant/detergent), preferably at a neutral pH-value, for example with 50 mM sodium phosphate, pH 7.0. It is possible to add to the buffers used, optionally, for increasing the washing efficiency, detergents, for example Tween 20™ (polysorbate 20), Triton® X 100 (octylphenoxypolyethoxyethanol) or chaotropic agents, for example guanidinium hydrochloride or urea. That washing step can be repeated a plurality of times depending on the sample material.

After separation of non-specifically bound material the membrane of the bound bacteria can be permeabilised or if necessary (depending on the detection assay used) destroyed by the addition of detergents (for example sodium dodecylsulphate, octylglucoside), chemicals (for example Polymyxin B), pore-forming polypeptides (for example Nisin, Holin, Mellitin) or proteins (for example Lysozyme). That membrane permeabilisation operation can be carried out for between 5 and 10 minutes at a temperature in the range of between about 100 and 50° C. The bound bacteria are then detected.

For detection of the bacteria bound to the bacteriophage tail proteins it is possible to use specific antibodies, bacteriophages or bacteriophage tail proteins. Preferably bacteriophages or bacteriophage tail proteins are used.

Specific bacteriophages or a combination of various bacteriophages can be used for the detection procedure if one or more bacteria species are to be specifically detected. For example the coliform bacteria present in a sample are bound by the immobilised bacteriophage tail proteins. Then, by means of specific bacteriophages, it is possible to detect individual bacteria species or a plurality of bacteria species can be detected by means of a combination of different bacteriophages. The bacteriophage tail proteins which are immobilised to the matrix are particularly preferably used in order to bind the bacteria to be detected. For the detection procedure, a marking, for example FITC, peroxidase or alkaline phosphatase, is coupled to the antibodies, bacteriophages or bacteriophage tail proteins, wherein signal development of the marking can be photometrically pursued after addition of a substrate. The genes for the bacteriophage tail proteins can be cloned in suitable expression vectors and in that way additionally modified according to the respective use involved, for example by fusion with a detection enzyme. Alternatively detection can be implemented by way of (bacterial) cellular enzymes (for example β-galactosidase in the case of coliforms) or also other cell constituents such as nucleic acids, proteins, lipids or sugar components.

Depending on the requirement involved for example fluorescence, luminescence, absorption or circular dichroism, conductivity or capacitance variations in the respective probes are detected in the appropriate standard measuring apparatuses. A calibration straight line can be implemented with suitable standard molecules for exact determination of concentration of the bacteria.

Detection of the bacteria bound to bacteriophage tail proteins can also be implemented by the use of a colorimetric test. In that case for example NADH, β-galactosidase activity or inorganic phosphate is detected. Those tests permit the detection of at least $10^4$ cells per ml, by using fluorescence dyes the level of sensitivity can be improved to between $10^2$ and $10^3$ cells per ml. The calorimetric tests can generally be used for detection of the activity of intracellular, membraneous or periplasmatic enzymes or cell constituents.

The calorimetric tests can be the same for all bacteria to be investigated, but they can also be specific for given bacteria/bacteriophage tail protein combinations. The choice of the marking for example of the enzyme or fluorescence marker used can be adapted to the respective bacteria genus or bacteria species under test.

A further aspect of the invention thus concerns a kit for the detection of bacteria, including a support with immobilised bacteriophage tail proteins and the solutions, with the assay reagents, which are necessary for detection of the bound bacteria. The supports can be all the above-described supports to which the bacteriophage tail proteins are immobilised as described above. The solutions with the assay reagents also correspond to the substances which are described for the detection of the bacteria in the method according to the invention. The kit can also optionally include washing solutions and enzymes or detergents which are required for breaking up the bacterial membrane.

The following examples explain the invention and are not to be considered as limiting it. Unless otherwise specified molecular-biological standard methods are employed, as described for example by Sambrook et al., 1989, Molecular cloning: A Laboratory Manual, second edition, Cold Spring Harbor Laboratory Press, Cold Spring Harbor, N.Y.

EXAMPLE 1

Isolation and Cloning of T4D p12, K3 p12 and T2 p12

T4D p12, K3 p12 and T2 p12 were isolated and cloned as described in Burda et al., 2000, Biol. Chem., Vol. 381, pp 255-258. T4D p12 was suitably cleaned up and used with Freund's adjuvant for the immunisation of rabbits. The polyclonal antiserum obtained detected both the T4D p12 and also the protease-resistant domain.

EXAMPLE 2

Protease Digestion of T4D p12 and Recombinant Production

The protease-resistant domain of p12 was obtained by protease digestion at various temperatures (see Chen & King, 1991, Danner et al., 1993) and then cleaned by conventional gel filtration chromatography. The N-terminus was determined by Edman decomposition and the C-terminus was analysed by mass spectrometry. For the DNA sequence of the domain obtained the terminal primers were furnished with a start and a stop codon. In a conventional PCR with the cDNA of the T4D p12 variant cDNA of the protease-resistant domain was amplified and then cloned into a vector. That mutant was then expressed in *E. coli* BL21 DE3 as a native trimer and isolated from the membrane fraction by EDTA extraction (see Burda & Miller, 1999, Eur. J. Biochem. 265, 771-778), the extractions being implemented in the presence of at least 100 mM EDTA.

EXAMPLE 3

Group-Specific Detection by Way of the Bacterial α-Galactosidase

For that purpose p12 (300 ng/well in 150 µl 100 mM PBS (4 mM $KH_2PO_4$, 16 mM $Na_2PO_4$, 115 mM NaCl); 96 well plate) was immobilised on a support system, a polystyrene microtiter plate, by adsorption at 37° C. in different periods of time (1 h, 2 h, 4 h, 16 h, 48 h) and the support was then blocked either with 1% BSA or 1% BSA, 0.5% Tween 20 in 100 mM PBS for 60 minutes. Various sample substances with bacteria (*E. coli* spec., *Citrobacter* spec., in LB-medium, milk or liquid manure) were incubated therewith (60 min, 370), then the sample was removed by washing with PBS (3-4× with 100 mM PBS, 0.5% Tween 20, in each case 250 µl for LB-medium, and milk, for liquid manure 4-6×) and the bound bacteria were detected by way of the bacterial β-galactosidase with β-Gal-Luminol (Tropix, Applied Biosystems) in accordance with the manufacturer's directions. Depending on the choice of substrate the assay permits a level of sensitivity of below 100 cells/ml in a total of less than 4 hours.

EXAMPLE 4

Group-Specific Detection by Way of Markers

For that purpose p12 (300 ng/well in 150 µl 100 mM PBS (4 mM $KH_2PO_4$, 16 mM $Na_2PO_4$, 115 mM NaCl); 96 well plate) was immobilised on a support system, a polystyrene microtiter plate, by adsorption at 37° C. in different periods of time (1 h, 2 h, 4 h, 16 h, 48 h) and the support was then blocked either with 1% BSA or 1% BSA, 0.5% Tween 20 in 100 mM PBS for 60 minutes. Various sample substances with bacteria (*E. coli* spec., *Citrobacter* spec., in LB-medium, milk or liquid manure) were incubated therewith (60 min, 370), then the sample was removed by washing with PBS (3-4× with 100 mM PBS, 0.5% Tween 20, in each case 250 µl for LB-medium, and milk, for liquid manure 4-6×). Then biotinylated phage tail protein was coupled to peroxidase coupled to streptavidin. That complex was given to the bound bacteria and incubated for various periods of time (10 min, 20 min, 30 min, 60 min). After washing, 3-4× with 100 mM PBS, 0.5% Tween 20, in each case 250 µl, the bound bacteria were detected using the ECL kit from Amersham in accordance with the manufacturer's directions. In that way below 1000 cells per ml were detected.

---

The invention claimed is:

1. A method for the detection of bacteria comprising the steps:
   a) coupling one or more species of isolated bacteriophage tail proteins onto a support;
   b) incubating said support coupled with said isolated bacteriophage tail proteins with a sample, whereby bacteria in said sample are bound to said bacteriophage tail proteins;
   c) contacting the bacteria bound to said isolated bacteriophage tail proteins with bacteriophages and/or bacteriophage proteins that bind specifically to the bacteria to be detected;
   d) removing bacteriophages and/or bacteriophage proteins not bound to the bacteria; and
   e) detecting the bound bacteria (i) by an enzyme coupled to said specifically bound bacteriophages and/or bacteriophage proteins, or (ii) by an immunoassay.

2. The method according to claim 1, wherein said isolated bacteriophage tail proteins are coupled to said support via adsorption, via chemical binding or via further proteins.

3. The method according to claim 1, wherein said isolated bacteriophage tail proteins are biotinylated and bound via Streptavidin or Streptavidin or Avidin variants.

4. The method according to claim 1, wherein said isolated bacteriophage tail proteins are T4 p12, T2 p12, K3 p12 or the short bacteriophage tail proteins of the phage Felix 01, P1 or PB1 or derivatives or fragments thereof.

5. The method according to claim 1, wherein said isolated bacteriophage tail proteins comprise the amino acid sequence according to SEQ ID NO:1 or 3.

6. The method according to claim 1, wherein said isolated bacteriophage tail proteins exhibit modifications.

7. The method according to claim 1, wherein said isolated bacteriophage tail proteins of one or more phage species detect at least two different bacterial species and/or genera.

8. The method according to claim 1, wherein said support is a microtiter plate, a test strip, slide, wafer, filter material or a flow through cell chamber, and composed of polystyrene, polypropylene, polycarbonate, polymethylmetaacrylate (PMMA), cellulose acetate, nitrocellulose, glass or silicium wafer.

9. The method according to claim 1, wherein the detection of bacteria is used in medicine, food industry and analytics, animal breeding, drinking water analytics or environmental analytics.

10. The method according to claim 1, further comprising the step, following step b) and preceding step c), of removing said sample and bacteria not bound to said isolated bacteriophage tail proteins.

11. The method of claim 1, wherein detecting the bound bacteria comprises detecting an enzyme previously coupled to said specifically bound bacteriophages.

12. The method of claim 1, wherein detecting the bound bacteria comprises an immunoassay.

13. A method for the detection of bacteria comprising the steps:
   a) coupling one or more species of isolated bacteriophage tail proteins onto a support;
   b) incubating said support coupled with said isolated bacteriophage tail proteins with a sample, whereby bacteria in said sample are bound to said isolated bacteriophage tail proteins;
   c) removing said sample from the bacteria not bound to said isolated bacteriophage tail proteins;
   d) adding substances which permeate or destroy the bacterial membrane, and
   e) detecting bound bacteria by bacterial cellular enzymes, nucleic acids, proteins, lipids or sugar residues.

14. The method according to claim 13, wherein the bacterial cellular enzyme is β-galactosidase.

15. The method according to claim 13, wherein said isolated bacteriophage tail proteins are coupled to said support via adsorption, via chemical binding or via further proteins.

16. The method according to claim 13, wherein said isolated bacteriophage tail proteins are biotinylated and bound via Streptavidin or Streptavidin or Avidin variants.

17. The method according to claim 13, wherein said isolated bacteriophage tail proteins are T4 p12, T2 p12, K3 p12 or the short isolated bacteriophage tail proteins of the phage Felix 01, P1 or PB1 or derivatives or fragments thereof.

18. The method according to claim 13, wherein said isolated bacteriophage tail proteins comprise the amino acid sequence according to SEQ ID NO:1 or 3.

19. The method according to claim 13, wherein said isolated bacteriophage tail proteins exhibit modifications.

20. The method according to claim 13, wherein said isolated bacteriophage tail proteins of one or more phage species detect at least two different bacterial species and/or genera.

21. The method according to claim 13, wherein said support is a microtiter plate, a test strip, slide, wafer, filter material or a flow through cell chamber, and composed of polystyrene, polypropylene, polycarbonate, polymethylmetaacrylate (PMMA), cellulose acetate, nitrocellulose, glass or silicium wafer.

22. The method according to claim 13, wherein the detection of bacteria is used in medicine, food industry and analytics, animal breeding, drinking water analytics or environmental analytics.

23. A kit comprising a support with immobilized isolated bacteriophage tail proteins and assay reagents for the detection of bound bacteria.

24. The kit according to claim 23, further comprising washing solutions and/or substances permeating or destroying the bacterial membrane.

25. An isolated polypeptide comprising the amino acid sequence of SEQ ID NO:3.

* * * * *

SEQUENCE LISTING

```
<160> NUMBER OF SEQ ID NOS: 4

<210> SEQ ID NO 1
<211> LENGTH: 527
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Met Ser Asn Asn Thr Tyr Gln His Val Ser Asn Glu Ser Arg Tyr Val
1               5                   10                  15

Lys Phe Asp Pro Thr Asp Thr Asn Phe Pro Pro Glu Ile Thr Asp Val
                20                  25                  30

His Ala Ala Ile Ala Ala Ile Ser Pro Ala Gly Val Asn Gly Val Pro
            35                  40                  45

Asp Ala Ser Ser Thr Thr Lys Gly Ile Leu Phe Leu Ala Thr Glu Gln
        50                  55                  60

Glu Val Ile Asp Gly Thr Asn Asn Thr Lys Ala Val Thr Pro Ala Thr
65                  70                  75                  80
```

```
Leu Ala Thr Arg Leu Ser Tyr Pro Asn Ala Thr Glu Ser Val Tyr Gly
                85                  90                  95
Leu Thr Arg Tyr Ser Thr Asp Asp Glu Ala Ile Ala Gly Val Asn Asn
            100                 105                 110
Glu Ser Ser Ile Thr Pro Ala Lys Phe Thr Val Ala Leu Asn Asn Val
        115                 120                 125
Phe Glu Thr Arg Val Ser Thr Glu Ser Ser Asn Gly Val Ile Lys Ile
    130                 135                 140
Ser Ser Leu Pro Gln Ala Leu Ala Gly Ala Asp Asp Thr Thr Ala Met
145                 150                 155                 160
Thr Pro Leu Lys Thr Gln Gln Leu Ala Val Lys Leu Ile Ala Gln Ile
                165                 170                 175
Ala Pro Ser Lys Asn Ala Ala Thr Glu Ser Glu Gln Gly Val Ile Gln
            180                 185                 190
Leu Ala Thr Val Ala Gln Ala Arg Gln Gly Thr Leu Arg Glu Gly Tyr
        195                 200                 205
Ala Ile Ser Pro Tyr Thr Phe Met Asn Ser Thr Ala Thr Glu Glu Tyr
    210                 215                 220
Lys Gly Val Ile Lys Leu Gly Thr Gln Ser Glu Val Asn Ser Asn Asn
225                 230                 235                 240
Ala Ser Val Ala Val Thr Gly Ala Thr Leu Asn Gly Arg Gly Ser Thr
                245                 250                 255
Thr Ser Met Arg Gly Val Val Lys Leu Thr Thr Thr Ala Gly Ser Gln
            260                 265                 270
Ser Gly Gly Asp Ala Ser Ser Ala Leu Ala Trp Asn Ala Asp Val Ile
        275                 280                 285
Gly Gln Arg Gly Gln Thr Ile Asn Gly Thr Leu Arg Ile Asn Asn
    290                 295                 300
Thr Leu Thr Ile Ala Ser Gly Ala Asn Ile Thr Gly Thr Val Asn
305                 310                 315                 320
Met Tyr Gly Gly Tyr Ile Gln Gly Lys Arg Val Val Thr Gln Asn Glu
                325                 330                 335
Ile Asp Arg Thr Ile Pro Val Gly Ala Ile Met Met Trp Ala Ala Asp
            340                 345                 350
Ser Leu Pro Ser Asp Ala Trp Arg Phe Cys His Gly Thr Val Ser
        355                 360                 365
Ala Ser Asp Cys Pro Leu Tyr Ala Ser Arg Ile Gly Thr Arg Tyr Gly
    370                 375                 380
Gly Ser Ser Ser Asn Pro Gly Leu Pro Asp Met Arg Gly Leu Phe Val
385                 390                 395                 400
Arg Gly Ser Gly Arg Gly Ser His Leu Thr Asn Pro Asn Val Asn Gly
                405                 410                 415
Asn Asp Gln Phe Gly Lys Pro Arg Leu Gly Val Gly Cys Thr Gly Gly
            420                 425                 430
Tyr Val Gly Glu Val Gln Lys Gln Gln Met Ser Tyr His Lys His Ala
        435                 440                 445
Gly Gly Phe Gly Glu Tyr Asp Asp Ser Gly Ala Phe Gly Asn Thr Arg
    450                 455                 460
Arg Ser Asn Phe Val Gly Thr Lys Gly Leu Asp Trp Asp Asn Arg
465                 470                 475                 480
Ser Tyr Phe Thr Asn Asp Gly Tyr Glu Ile Asp Pro Ala Ser Gln Arg
                485                 490                 495
Asn Ser Arg Tyr Thr Leu Asn Arg Pro Glu Leu Ile Gly Asn Glu Thr
```

```
                    500             505             510
Arg Pro Trp Asn Ile Ser Leu Asn Tyr Ile Ile Lys Val Lys Glu
        515             520             525

<210> SEQ ID NO 2
<211> LENGTH: 1578
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
agtaataata catatcaaca cgtttctaat gaatctcgtt atgtaaaatt tgatcctacc      60
gatacgaatt ttccaccgga gattactgat gttcacgctg ctatagcagc catttctcct     120
gctggcgtaa atggagttcc tgatgcatcg tcaacaacaa agggaatttt atttcttgcc     180
actgaacagg aagttataga tggaactaat aataccaaag cagttacacc agcaacgttg     240
gcaacaagat tatcatatcc aaacgcaact gaaagtgttt acggattaac aagatattca     300
accgatgatg aagccattgc cggagttaat aatgaatctt ctataactcc agctaaattt     360
actgttgctc ttaataatgt ttttgaaact cgtgtttcaa ctgaatcatc aaatggggtt     420
attaaaattt catctttacc gcaagcattg gcaggtgcag atgatactac tgcaatgact     480
ccattaaaaa cacaacaatt agctgttaaa ttgattgcgc aaattgctcc ttctaaaaat     540
gctgctacag aatctgagca aggtgtaatt cagttagcta cagtagcaca ggctcgtcag     600
ggaactttaa gagaaggata cgcaatttct ccttatacgt ttatgaattc tactgctact     660
gaagaatata aaggcgtaat taaattagga acgcaatcag aagttaactc gaataatgct     720
tctgttgcgg ttactggagc aactcttaat ggtcgtggtt ctacgacgtc aatgagaggc     780
gtagttaaat taactacaac cgccggttca cagagtggag gcgatgcttc atcagcctta     840
gcttggaatg ctgacgttat ccaccaaaga ggcggtcaaa ctattaatgg aacacttcgc     900
attaataata cgcttacaat agcttcaggt ggggcaaata ttaccggaac agttaacatg     960
actggcggtt atattcaagg taaacgcgtc gtaacacaaa atgaaattga tagaactatt    1020
cctgtcggag ctattatgat gtgggccgct gatagtcttc ctagtgatgc ttggcgtttt    1080
tgccacggtg gaactgtttc agcgtcagat tgtccattat atgcttctag aattggaaca    1140
agatatggcg gaagctcatc aaatcctgga ttgcctgaca tgcgcggtct ttttgttcgt    1200
ggctctggcc gtggctctca tttaacaaat ccaaatgtta atggtaatga ccaatttggt    1260
aaacctagat taggtgtagg ttgtactggt ggatatgttg gtgaagtaca gaaacaacag    1320
atgtcttatc ataaacatgc tggtggattt ggtgagtatg atgattctgg ggcattcggt    1380
aatactcgta gatcaaattt tgttggtaca cgtaaaggac ttgactggga taaccgttca    1440
tacttcacta tgacgggta tgaaattgac ccagcatcac aacgaaattc cagatataca    1500
ttaaatcgtc ctgaattaat tggaaatgaa acacgtccat ggaacatttc tttaaactac    1560
ataattaagg taaaagaa                                                  1578

<210> SEQ ID NO 3
<211> LENGTH: 317
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3
```

```
Leu Ser Tyr Pro Asn Ala Thr Glu Ser Val Tyr Gly Leu Thr Arg Tyr
  1               5                  10                  15

Ser Thr Asp Asp Glu Ala Ile Ala Gly Val Asn Asn Glu Ser Ser Ile
             20                  25                  30

Thr Pro Ala Lys Phe Thr Val Ala Leu Asn Asn Val Phe Glu Thr Arg
         35                  40                  45

Val Ser Thr Glu Ser Ser Asn Gly Val Ile Lys Ile Ser Ser Leu Pro
     50                  55                  60

Gln Ala Leu Ala Gly Ala Asp Asp Thr Thr Ala Met Thr Pro Leu Lys
 65              70                  75                  80

Thr Gln Gln Leu Ala Val Lys Leu Ile Ala Gln Ile Ala Pro Ser Lys
                 85                  90                  95

Asn Ala Ala Thr Glu Ser Glu Gln Gly Val Ile Gln Leu Ala Thr Val
                100                 105                 110

Ala Gln Ala Arg Gln Gly Thr Leu Arg Glu Gly Tyr Ala Ile Ser Pro
            115                 120                 125

Tyr Thr Phe Met Asn Ser Thr Ala Thr Glu Glu Tyr Lys Gly Val Ile
        130                 135                 140

Lys Leu Gly Thr Gln Ser Glu Val Asn Ser Asn Ala Ser Val Ala
145                 150                 155                 160

Val Thr Gly Ala Thr Leu Asn Gly Arg Gly Ser Thr Thr Ser Met Arg
                165                 170                 175

Gly Val Val Lys Leu Thr Thr Thr Ala Gly Ser Gln Ser Gly Gly Asp
            180                 185                 190

Ala Ser Ser Ala Leu Ala Trp Asn Ala Asp Val Ile His Gln Arg Gly
        195                 200                 205

Gly Gln Thr Ile Asn Gly Thr Leu Arg Ile Asn Asn Thr Leu Thr Ile
    210                 215                 220

Ala Ser Gly Gly Ala Asn Ile Thr Gly Thr Val Asn Met Thr Gly Gly
225                 230                 235                 240

Tyr Ile Gln Gly Lys Arg Val Val Thr Gln Asn Glu Ile Asp Arg Thr
                245                 250                 255

Ile Pro Val Gly Ala Ile Met Met Trp Ala Ala Asp Ser Leu Pro Ser
                260                 265                 270

Asp Ala Trp Arg Phe Cys His Gly Gly Thr Val Ser Ala Ser Asp Cys
            275                 280                 285

Pro Leu Tyr Ala Ser Arg Ile Gly Thr Arg Tyr Gly Gly Ser Ser Ser
        290                 295                 300

Asn Pro Gly Leu Pro Asp Met Arg Gly Leu Phe Val Arg
305                 310                 315

<210> SEQ ID NO 4
<211> LENGTH: 951
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
ttatcatatc caaacgcaac tgaaagtgtt tacggattaa caagatattc aaccgatgat    60
gaagccattg ccggagttaa taatgaatct tctataactc cagctaaatt tactgttgct   120
cttaataatg tttttgaaac tcgtgtttca actgaatcat caaatggggt tattaaaatt   180
tcatctttac cgcaagcatt ggcaggtgca gatgatacta ctgcaatgac tccattaaaa   240
```

-continued

```
acacaacaat tagctgttaa attgattgcg caaattgctc cttctaaaaa tgctgctaca    300
gaatctgagc aaggtgtaat tcagttagct acagtagcac aggctcgtca gggaacttta    360
agagaaggat acgcaatttc tccttatacg tttatgaatt ctactgctac tgaagaatat    420
aaaggcgtaa ttaaattagg aacgcaatca gaagttaact cgaataatgc ttctgttgcg    480
gttactggag caactcttaa tggtcgtggt tctacgacgt caatgagagg cgtagttaaa    540
ttaactacaa ccgccggttc acagagtgga ggcgatgctt catcagcctt agcttggaat    600
gctgacgtta tccaccaaag aggcggtcaa actattaatg gaacacttcg cattaataat    660
acgcttacaa tagcttcagg tggggcaaat attaccggaa cagttaacat gactggcggt    720
tatattcaag gtaaacgcgt cgtaacacaa aatgaaattg atagaactat tcctgtcgga    780
gctattatga tgtgggccgc tgatagtctt cctagtgatg cttggcgttt ttgccacggt    840
ggaactgttt cagcgtcaga ttgtccatta tatgcttcta gaattggaac aagatatggc    900
ggaagctcat caaatcctgg attgcctgac atgcgcggtc tttttgttcg t             951
```